US011542320B2

(12) United States Patent
Liu et al.

(10) Patent No.: US 11,542,320 B2
(45) Date of Patent: Jan. 3, 2023

(54) NUCLEIC ACIDS ENCODING SINGLE DOMAIN ANTIBODIES TO CHIKUNGUNYA VIRUS

(71) Applicant: The Government of the United States of America, as represented by the Secretary of the Navy, Arlington, VA (US)

(72) Inventors: Jinny Lin Liu, Ellicott City, MD (US); George P. Anderson, Bowie, MD (US); Ellen R. Goldman, Germantown, MD (US)

(73) Assignee: The Government of the United States of Americas, as represented by the Secretary of the Navy, Washington, DC (US)

( * ) Notice: Subject to any disclaimer, the term of this patent is extended or adjusted under 35 U.S.C. 154(b) by 32 days.

(21) Appl. No.: 17/245,180

(22) Filed: Jul. 9, 2021

(65) Prior Publication Data

US 2021/0347863 A1      Nov. 11, 2021

Related U.S. Application Data

(62) Division of application No. 16/513,881, filed on Jul. 17, 2019, now Pat. No. 11,028,152.

(60) Provisional application No. 62/701,301, filed on Jul. 20, 2018.

(51) Int. Cl.
| | | |
|---|---|---|
| *C07K 16/10* | (2006.01) | |
| *A61P 31/14* | (2006.01) | |
| *G01N 33/569* | (2006.01) | |

(52) U.S. Cl.
CPC .......... *C07K 16/1081* (2013.01); *A61P 31/14* (2018.01); *G01N 33/56983* (2013.01); *C07K 2317/22* (2013.01); *C07K 2317/569* (2013.01); *C07K 2317/76* (2013.01); *C07K 2317/92* (2013.01); *C12N 2770/36111* (2013.01); *C12N 2770/36123* (2013.01); *G01N 2333/181* (2013.01)

(58) Field of Classification Search
CPC .......... C07K 2317/569; C12N 16/1081; C12N 2770/36111
See application file for complete search history.

(56) References Cited

U.S. PATENT DOCUMENTS

2016/0145323 A1    5/2016   Doranz et al.

OTHER PUBLICATIONS

Yathi, K. K., et al., 2013, Determination of B cell epitopes and evaluation of antigen capture ELISA for the earlier diagnosis of CHIK virus using anti-rCHIK E1 rabbit antibodies, J. Immunol. Meth. 393:45-52.*
Singh, P., et al., Aug. 2013, Current research and clinical trials for a vaccine against Chikungunya virus, Vaccine: Develop. Ther. 3:35-46.
Burt, F. J., et al., Apr. 2017, Chikungunya virus: an update on the biology and pathogenesis of this emerging pathogen, Lancet Infect. Dis. 17:e017-17.
Kumar, R., et al., Feb. 2020, Antibody-based therapeutic interventions: possible strategy to count chikungunya viral infection, Applied Microbial. Biotechnol. 104:3209-3228.
Pal P, Dowd KA, Brien JD, Edeling MA, Gorlatov S, et al. (2013) Development of a Highly Protective Combination Monoclonal Antibody Therapy against Chikungunya Virus. PLoS Pathog 9(4): e1003312. doi:10.1371/journal.ppat.1003312.
Rebecca Broeckel R, Fox JM, Haese N, Kreklywich CN, Sukulpovi-Petty S, et al. Therapeutic administration of a recombinant human monoclonal antibody reduces the severity of chikungunya virus disease in rhesus macaques PLoS Negi Trop Dis 11(6): e0005637, 2017.
Warter L, Lee CY, Thiagarajan R, Grandadam M, Lebecque S, et al. Chikungunya Virus Envelope-Specific Human Monoclonal Antibodies with Broad Neutralization Potency J Immunol 186 (5), 2011.

* cited by examiner

*Primary Examiner* — Jeffrey S Parkin
(74) *Attorney, Agent, or Firm* — U S Naval Research Laboratory; Roy Roberts

(57) ABSTRACT

Described herein are nucleic acids encoding single-domain antibodies that might serve as alternatives to conventional monoclonal antibodies for either the detection or treatment of Chikungunya Virus (CHIKV).

3 Claims, 9 Drawing Sheets

Specification includes a Sequence Listing.

SEQUENCE LISTING

```
<160> NUMBER OF SEQ ID NOS: 16

<210> SEQ ID NO 1
<211> LENGTH: 113
<212> TYPE: PRT
<213> ORGANISM: Artificial Sequence
<220> FEATURE:
<223> OTHER INFORMATION: synthetic construct

<400> SEQUENCE: 1

Glu Val Gln Leu Gln Ala Ser Gly Gly Gly Ser Val Gln Ala Gly Gly
1               5                   10                  15

Ser Leu Arg Leu Ser Cys Val Thr Ser Gln Asn Leu Phe Glu Tyr Tyr
            20                  25                  30

Thr Met Gly Trp Tyr Arg Gln Val Pro Gly Ser Gln Arg Glu Arg Val
        35                  40                  45

Ala Leu Ile Asn Asn Gly Gly Ser Thr Val Ala Gly Ser Val Glu Gly
    50                  55                  60

Arg Phe Thr Ile Ser Arg Asp His Ala Lys Asn Ser Val Tyr Leu Gln
65                  70                  75                  80

Met Asn Tyr Leu Lys Pro Glu Asp Ser Ala Val Tyr Tyr Cys Arg Ala
                85                  90                  95

Phe Gly Pro Ala Asp Tyr Trp Gly Gln Gly Thr Gln Val Thr Val Ser
            100                 105                 110

Ser

<210> SEQ ID NO 2
<211> LENGTH: 113
<212> TYPE: PRT
<213> ORGANISM: Artificial Sequence
<220> FEATURE:
<223> OTHER INFORMATION: synthetic construct

<400> SEQUENCE: 2

Glu Val Gln Leu Gln Ala Ser Gly Gly Gly Leu Val Gln Pro Gly Gly
1               5                   10                  15

Ser Leu Arg Leu Ser Cys Val Ala Ser Gln Asn Leu Phe Glu Tyr Tyr
            20                  25                  30

Thr Met Gly Trp Tyr Arg Gln Val Pro Gly Ser Gln Arg Glu Arg Val
        35                  40                  45

Ala Leu Ile Asn Asn Gly Gly Ser Asn Val Ala Gly Ser Val Glu Gly
    50                  55                  60

Arg Phe Thr Ile Ser Arg Asp Asn Thr Lys Asn Ser Ile Tyr Leu Gln
65                  70                  75                  80

Met Asn Asn Leu Lys Pro Glu Asp Ser Ala Val Tyr Tyr Cys Arg Ala
                85                  90                  95

Phe Gly Pro Ala Asp Tyr Trp Gly Gln Gly Thr Gln Val Thr Val Ser
            100                 105                 110

Ser

<210> SEQ ID NO 3
<211> LENGTH: 113
```

```
<212> TYPE: PRT
<213> ORGANISM: Artificial Sequence
<220> FEATURE:
<223> OTHER INFORMATION: synthetic construct

<400> SEQUENCE: 3

Glu Val Gln Leu Gln Ala Ser Gly Gly Gly Ser Val Gln Ala Gly Gly
1               5                   10                  15

Ser Leu Arg Leu Ser Cys Val Ala Ser Gln Asn Leu Phe Glu Tyr Tyr
            20                  25                  30

Thr Met Gly Trp Tyr Arg Gln Val Pro Gly Ser Gln Arg Glu Arg Val
        35                  40                  45

Ala Leu Ile Asn Asn Gly Asp Ser Asn Val Ala Gly Ser Val Glu Gly
    50                  55                  60

Arg Phe Thr Ile Ser Arg Asp Asn Ala Lys Asn Ser Ile Tyr Leu Gln
65                  70                  75                  80

Met Asn Asn Leu Lys Pro Glu Asp Ser Ala Val Tyr Tyr Cys Arg Ala
                85                  90                  95

Phe Gly Pro Ala Asp Tyr Trp Gly Gln Gly Thr Gln Val Thr Val Ser
            100                 105                 110

Ser

<210> SEQ ID NO 4
<211> LENGTH: 113
<212> TYPE: PRT
<213> ORGANISM: Artificial Sequence
<220> FEATURE:
<223> OTHER INFORMATION: synthetic construct

<400> SEQUENCE: 4

Glu Val Gln Leu Gln Ala Ser Gly Gly Gly Ser Val Gln Ala Gly Gly
1               5                   10                  15

Ser Leu Arg Leu Ser Cys Val Ala Ser Gln Asn Leu Phe Glu Tyr Tyr
            20                  25                  30

Thr Met Gly Trp Tyr Arg Gln Val Pro Gly Ser Gln Arg Glu Arg Val
        35                  40                  45

Ala Leu Ile Asn Asn Gly Gly Ser Asn Val Ala Gly Ser Val Glu Gly
    50                  55                  60

Arg Phe Thr Ile Ser Arg Asp Asn Ala Lys Asn Ser Ile Tyr Leu Gln
65                  70                  75                  80

Met Asn Asn Leu Lys Pro Glu Asp Ser Ala Val Tyr Tyr Cys Arg Ala
                85                  90                  95

Phe Gly Pro Ala Asp Tyr Trp Gly Gln Gly Thr Gln Val Thr Val Ser
            100                 105                 110

Ser

<210> SEQ ID NO 5
<211> LENGTH: 113
<212> TYPE: PRT
<213> ORGANISM: Artificial Sequence
<220> FEATURE:
<223> OTHER INFORMATION: synthetic construct

<400> SEQUENCE: 5

Glu Val Gln Leu Gln Ala Ser Gly Gly Gly Ser Val Gln Ala Gly Gly
1               5                   10                  15

Ser Leu Arg Leu Ser Cys Val Ala Ser Gln Asn Leu Phe Glu Tyr Tyr
            20                  25                  30
```

Thr Met Gly Trp Tyr Arg Gln Val Pro Gly Ser Gln Arg Glu Arg Val
            35                  40                  45

Ala Leu Ile Asn Asn Gly Gly Ser Asn Val Ala Gly Pro Val Glu Gly
     50                  55                  60

Arg Phe Thr Ile Ser Arg Asp Asn Ala Lys Asn Ser Ile Tyr Leu Gln
 65                  70                  75                  80

Met Asn Asn Leu Lys Pro Glu Asp Ser Ala Val Tyr Tyr Cys Arg Ala
                 85                  90                  95

Phe Gly Pro Ala Asp Tyr Trp Gly Gln Gly Thr Gln Val Thr Val Ser
                100                 105                 110

Thr

<210> SEQ ID NO 6
<211> LENGTH: 113
<212> TYPE: PRT
<213> ORGANISM: Artificial Sequence
<220> FEATURE:
<223> OTHER INFORMATION: synthetic construct

<400> SEQUENCE: 6

Glu Val Gln Leu Gln Ala Ser Gly Gly Gly Ser Val Gln Ala Gly Gly
 1               5                  10                  15

Thr Leu Arg Leu Ser Cys Val Ser Ser Gln Asn Leu Phe Glu Tyr Tyr
            20                  25                  30

Thr Met Ser Trp Tyr Arg Gln Val Pro Gly Ser Gln Arg Glu Arg Val
            35                  40                  45

Ala Leu Ile Asn Asn Gly Gly Ser Asp Val Ala Gly Ser Val Glu Gly
     50                  55                  60

Arg Phe Thr Ile Ser Arg Asp Asn Ala Lys Asn Ser Ile Tyr Leu Gln
 65                  70                  75                  80

Met Asn Asn Leu Lys Pro Glu Asp Ser Ala Val Tyr Tyr Cys Arg Ala
                 85                  90                  95

Phe Gly Pro Ala Asp Tyr Trp Gly Gln Gly Thr Gln Val Thr Val Ser
                100                 105                 110

Ser

<210> SEQ ID NO 7
<211> LENGTH: 113
<212> TYPE: PRT
<213> ORGANISM: Artificial Sequence
<220> FEATURE:
<223> OTHER INFORMATION: synthetic construct

<400> SEQUENCE: 7

Glu Val Gln Leu Gln Ala Ser Gly Gly Gly Ser Val Gln Ala Gly Gly
 1               5                  10                  15

Ser Leu Arg Leu Ser Cys Val Ser Ser Gln Asn Leu Leu Glu Tyr Tyr
            20                  25                  30

Thr Met Gly Trp Tyr Arg Gln Val Pro Gly Ser Gln Arg Glu Arg Val
            35                  40                  45

Ala Leu Ile Asn Asn Gly Gly Ser Asn Val Ala Gly Ser Val Glu Gly
     50                  55                  60

Arg Phe Thr Ile Ser Arg Asp Asn Ala Lys Asn Ser Ile Tyr Leu Gln
 65                  70                  75                  80

Met Asn Asn Leu Lys Pro Glu Asp Ser Ala Val Tyr Tyr Cys Arg Ala
                 85                  90                  95

Phe Gly Pro Ala Asp Tyr Trp Gly Gln Gly Thr Gln Val Thr Val Ser

Ser

<210> SEQ ID NO 8
<211> LENGTH: 125
<212> TYPE: PRT
<213> ORGANISM: Artificial Sequence
<220> FEATURE:
<223> OTHER INFORMATION: synthetic construct

<400> SEQUENCE: 8

Asp Val Gln Leu Gln Ala Ser Gly Gly Gly Leu Val Gln Ala Gly Gly
1               5                   10                  15

Thr Leu Arg Leu Ser Cys Ala His Ser Gly Arg Thr Ser Ser Thr Gln
            20                  25                  30

Phe Trp Gly Trp Phe Arg Gln Ala Pro Gly Lys Glu Arg Glu Phe Val
        35                  40                  45

Ala Gly Met Ser Arg Ser Gly Leu Ser Thr Phe Tyr Ala Asp Ser Val
    50                  55                  60

Lys Gly Arg Phe Ala Ile Ser Arg Asp Ser Gly Lys Asn Thr Val Tyr
65                  70                  75                  80

Leu Gln Met Asn Ser Leu Lys Pro Glu Asp Thr Ala Val Tyr Phe Cys
                85                  90                  95

Ala Ser Ser Pro Phe Ile Gly Glu His Tyr Tyr Ser Ser Thr Lys Tyr
            100                 105                 110

His Tyr Trp Gly Gln Gly Thr Gln Val Thr Val Ser Ser
        115                 120                 125

<210> SEQ ID NO 9
<211> LENGTH: 125
<212> TYPE: PRT
<213> ORGANISM: Artificial Sequence
<220> FEATURE:
<223> OTHER INFORMATION: synthetic construct

<400> SEQUENCE: 9

Glu Val Gln Leu Gln Ala Ser Gly Gly Gly Leu Val Gln Ala Gly Gly
1               5                   10                  15

Thr Leu Arg Leu Ser Cys Ala His Ser Gly Arg Thr Ser Ser Thr Gln
            20                  25                  30

Phe Trp Gly Trp Phe Arg Gln Ala Pro Gly Lys Glu Arg Glu Phe Val
        35                  40                  45

Ala Gly Met Ser Arg Ser Gly Leu Ser Thr Phe Tyr Ala Asp Ser Val
    50                  55                  60

Lys Gly Arg Phe Ala Ile Ser Arg Asp Asn Gly Lys Asn Thr Val Tyr
65                  70                  75                  80

Leu Gln Met Asn Ser Leu Lys Pro Glu Asp Thr Ala Val Tyr Phe Cys
                85                  90                  95

Ala Ser Ser Pro Phe Ile Gly Glu His Tyr Tyr Ser Ser Thr Lys Tyr
            100                 105                 110

His Tyr Trp Gly Gln Gly Thr Gln Val Thr Val Ser Ser
        115                 120                 125

<210> SEQ ID NO 10
<211> LENGTH: 125
<212> TYPE: PRT
<213> ORGANISM: Artificial Sequence
<220> FEATURE:
<223> OTHER INFORMATION: synthetic construct

<400> SEQUENCE: 10

Asp Val Gln Leu Gln Ala Ser Gly Gly Gly Leu Val Gln Ala Gly Gly
1               5                   10                  15

Thr Leu Arg Leu Ser Cys Ala His Ser Gly Arg Thr Ser Ser Thr Gln
            20                  25                  30

Phe Trp Gly Trp Phe Arg Gln Ala Pro Gly Lys Glu Arg Glu Phe Val
        35                  40                  45

Ala Gly Met Ser Arg Ser Gly Leu Ser Thr Phe Tyr Ala Asp Ser Val
    50                  55                  60

Lys Gly Arg Phe Ala Ile Ser Arg Asp Asn Gly Lys Asn Thr Val Tyr
65                  70                  75                  80

Leu Gln Met Asn Ser Leu Lys Pro Glu Asp Thr Ala Val Tyr Phe Cys
                85                  90                  95

Ala Ser Ser Pro Phe Ile Gly Glu His Tyr Tyr Ser Thr Lys Tyr
            100                 105                 110

His Tyr Trp Gly Gln Gly Thr Gln Val Thr Val Ser Ser
        115                 120                 125

<210> SEQ ID NO 11
<211> LENGTH: 125
<212> TYPE: PRT
<213> ORGANISM: Artificial Sequence
<220> FEATURE:
<223> OTHER INFORMATION: synthetic construct

<400> SEQUENCE: 11

Glu Val Gln Leu Gln Ala Ser Gly Gly Gly Leu Val Gln Ala Gly Gly
1               5                   10                  15

Thr Leu Arg Leu Ser Cys Ala His Ser Gly Arg Thr Ser Ser Thr Gln
            20                  25                  30

Phe Trp Gly Trp Phe Arg Arg Ala Pro Gly Lys Glu Arg Glu Phe Val
        35                  40                  45

Ala Gly Met Ser Arg Ser Gly Leu Ser Thr Phe Tyr Ala Asp Ser Val
    50                  55                  60

Lys Gly Arg Phe Ala Ile Ser Arg Asp Asn Gly Lys Asn Thr Val Tyr
65                  70                  75                  80

Leu Gln Met Asn Ser Leu Lys Pro Glu Asp Thr Ala Val Tyr Phe Cys
                85                  90                  95

Ala Ser Ser Pro Phe Ile Gly Glu His Tyr Tyr Ser Ser Arg Lys Tyr
            100                 105                 110

His Tyr Trp Gly Gln Gly Thr Gln Val Thr Val Ser Ser
        115                 120                 125

<210> SEQ ID NO 12
<211> LENGTH: 123
<212> TYPE: PRT
<213> ORGANISM: Artificial Sequence
<220> FEATURE:
<223> OTHER INFORMATION: synthetic construct

<400> SEQUENCE: 12

Glu Val Gln Leu Gln Ala Ser Gly Gly Gly Leu Val Gln Ala Gly Gly
1               5                   10                  15

Ser Leu Arg Leu Ser Cys Ala Ala Ser Gln Asn Ile Phe Ser Ile Asn
            20                  25                  30

Val Met Gly Trp Tyr Arg Gln Ala Pro Gly Glu Gln Arg Glu Leu Val
        35                  40                  45

```
Ala Ala Ile Thr Ser Gly Gly Ser Thr Asn Val Ala Asp Ser Val Lys
        50                  55                  60

Gly Arg Val Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Glu Glu Thr Tyr Tyr Ser Gly Ser Tyr Tyr Gly Asp Met Glu Tyr
            100                 105                 110

Trp Gly Gln Gly Thr Gln Ala Thr Val Ser Ser
            115                 120

<210> SEQ ID NO 13
<211> LENGTH: 121
<212> TYPE: PRT
<213> ORGANISM: Artificial Sequence
<220> FEATURE:
<223> OTHER INFORMATION: synthetic construct

<400> SEQUENCE: 13

Glu Val Gln Leu Gln Ala Ser Gly Gly Gly Leu Val Arg Pro Gly Gly
1               5                   10                  15

Ser Leu Arg Leu Ser Cys Ala Ala Ser Gly Ser Phe Phe Thr Ile Asp
            20                  25                  30

Thr Met Ala Trp Tyr Arg Gln Ala Pro Gly Arg Arg Arg Glu Leu Val
        35                  40                  45

Ala Arg Gln Ser Ser Gly Arg Ser Pro Asp Tyr Asp Asp Ser Val Val
    50                  55                  60

Gly Arg Phe Thr Ile Ser Arg Asp Ile Ala Lys Ser Ser Val Tyr Leu
65                  70                  75                  80

Gln Met Asp Ser Leu Gln Pro Glu Asp Thr Ala Leu Tyr Tyr Cys Tyr
                85                  90                  95

Gln Ser Ile Arg Pro Trp Pro Gly Ser Ser Tyr Glu Ala His Trp Gly
            100                 105                 110

Gln Gly Ile Gln Val Ile Val Ser Ser
            115                 120

<210> SEQ ID NO 14
<211> LENGTH: 121
<212> TYPE: PRT
<213> ORGANISM: Artificial Sequence
<220> FEATURE:
<223> OTHER INFORMATION: synthetic construct

<400> SEQUENCE: 14

Glu Val Gln Leu Gln Ala Ser Gly Gly Gly Leu Val Gln Pro Gly Gly
1               5                   10                  15

Ser Leu Arg Leu Ser Cys Ala Ala Ser Gly Ser Phe Phe Thr Ile Asp
            20                  25                  30

Thr Met Ala Trp Tyr Arg Gln Ala Pro Gly Lys Gln Arg Glu Leu Val
        35                  40                  45

Ala Arg Gln Ser Ser Gly Arg Ser Pro Asp Tyr Asp Asp Ser Val Val
    50                  55                  60

Gly Arg Phe Thr Ile Ser Arg Asp Ile Ala Lys Ser Ser Val Cys Leu
65                  70                  75                  80

Gln Met Asp Ser Leu Gln Pro Glu Asp Thr Ala Leu Tyr Tyr Cys Tyr
                85                  90                  95

Gln Ser Ile Arg Pro Trp Pro Gly Ser Ser Tyr Glu Ala His Trp Gly
```

```
                    100                 105                 110

Gln Gly Ile Gln Val Ile Val Ser Ser
        115                 120

<210> SEQ ID NO 15
<211> LENGTH: 125
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (103)..(112)
<223> OTHER INFORMATION: Xaa can be any naturally occurring amino acid

<400> SEQUENCE: 15

Glu Val Gln Leu Gln Ala Ser Gly Gly Gly Leu Val Gln Ala Gly Gly
1               5                   10                  15

Ser Leu Arg Leu Ser Cys Val Ala Ser Gln Asn Leu Phe Glu Tyr Tyr
            20                  25                  30

Thr Met Gly Trp Xaa Arg Gln Val Pro Gly Ser Xaa Arg Glu Arg Val
        35                  40                  45

Ala Leu Ile Asn Asn Gly Gly Xaa Xaa Ser Xaa Val Ala Gly Ser Val
    50                  55                  60

Glu Gly Arg Phe Thr Ile Ser Arg Asp Asn Ala Lys Asn Ser Xaa Tyr
65                  70                  75                  80

Leu Gln Met Xaa Xaa Leu Lys Pro Glu Asp Ser Ala Val Tyr Xaa Cys
                85                  90                  95

Arg Ala Phe Gly Pro Ala Xaa Xaa Xaa Xaa Xaa Xaa Xaa Xaa Xaa
            100                 105                 110

Asp Tyr Met Gly Gln Gly Thr Gln Val Thr Val Ser Ser
        115                 120                 125

<210> SEQ ID NO 16
<211> LENGTH: 124
<212> TYPE: PRT
<213> ORGANISM: Artificial Sequence
<220> FEATURE:
<223> OTHER INFORMATION: synthetic construct
<220> FEATURE:
```

```
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (98)..(112)
<223> OTHER INFORMATION: Xaa can be any naturally occurring amino acid

<400> SEQUENCE: 16

Xaa Val Gln Leu Gln Ala Ser Gly Gly Gly Leu Val Gln Ala Gly Gly
 1               5                  10                  15

Ser Leu Arg Leu Ser Cys Ala Ala Ser Gln Asn Xaa Phe Xaa Xaa Thr
            20                  25                  30

Met Gly Trp Xaa Arg Gln Ala Pro Gly Xaa Gln Arg Glu Xaa Val Ala
        35                  40                  45

Xaa Ile Xaa Xaa Ser Gly Gly Ser Xaa Xaa Val Ala Asp Ser Val Xaa
    50                  55                  60

Gly Arg Phe Thr Ile Ser Arg Asp Xaa Ala Lys Asn Ser Xaa Tyr Leu
```

```
                65                  70                  75                  80
Gln Met Xaa Ser Leu Lys Pro Glu Asp Thr Ala Val Tyr Xaa Cys Xaa
                    85                  90                  95

Ala Xaa Xaa Xaa Xaa Xaa Xaa Xaa Xaa Xaa Xaa Xaa Xaa Xaa Xaa Xaa
                100                 105                 110

Tyr Met Gly Gln Gly Thr Gln Val Thr Val Ser Ser
                115                 120
```

NUCLEIC ACIDS ENCODING SINGLE DOMAIN ANTIBODIES TO CHIKUNGUNYA VIRUS

CROSS-REFERENCE TO RELATED APPLICATIONS

This application claims the benefit of U.S. Provisional Application 62/701,301 filed on Jul. 20, 2019 and is a division of U.S. patent application Ser. No. 16/513,881 filed on Jul. 19, 2020, the entirety of each of which is incorporated herein by reference.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375, USA; +1.202.767.7230; techtran@nrl.navy.mil, referencing NC 108,380.

BACKGROUND

Chikungunya virus (CHIKV) is a mosquito-transmitted alphavirus that causes outbreaks of polyarthritis in humans, and is currently a threat to spread to the United States due to the presence of its mosquito vector, *Aedes albopictus*.

CHIKV, like other alphaviruses, has a single-stranded positive sense RNA genome of about 11.8 kb encoding two polyproteins: one nonstructural polyprotein that produces four nonstructural proteins involved in genome replication, capping and polyprotein processing and the other structural polyprotein that produces the capsid as well as the E2 and E1 envelope glycoproteins. Virions are produced in the cytoplasm of the infected cells and later are enveloped and budded out of the membrane. Each virion is composed of the genomic RNA with 240 copies of the capsid protein and 240 copies of E1/E2 heterodimers embedded in the membrane. There are 80 trimeric E1/E2 spikes projecting outward from the membrane and the tip of each complex is formed by E2 protein that interacts with the cell receptor. E2 is the target of the most CHIKV-neutralizing antibodies.

Chikungunya virus-like particles (VLPs) are produced by encoding E1/E2 structural proteins with or without capsid proteins from the recombinant plasmids containing the sequences identical to the 3' region of the genomic RNA. They have been shown to effectively generate immunity in animals and non-human primates. VLPs are a promising vaccine candidate that could provide for the long term solution to CHIKV infection. In addition to developing vaccines, the development of effective small molecule therapeutics and rapid low cost methods for diagnosis are also critical to limiting the severity of the disease and hopefully reducing the long term health effects. Antibody-based therapeutics are being investigated as a way to bridge the gap until an effective immune response occurs. Antibodies can also play a role in the diagnosis of CHIKV infection, as lower cost rapid alternatives to RT-PCR methods.

To date most antibodies investigated for therapeutic or detection applications have been conventional IgGs. As therapeutics, there is the concern with their use, as antibodies are known to exacerbate the illness through an Fc mediated process. As diagnostics, it would be desirable that they be robust enough to be utilized in point-of-care (POC) assays where maintaining a cold chain becomes problematic It is not believed that a human vaccine or therapeutic is currently available to protect against CHIKV infection. A need exists for techniques to detect CHIKV infection and for an effective therapeutic against the virus.

BRIEF SUMMARY

In one embodiment, an isolated includes a protein sequence selected from the group consisting of SEQ ID Nos. 1-14.

In another embodiment, a method of detecting Chikungunya virus includes analyzing a sample known or suspected to contain Chikungunya virus using an immunoassay comprising an antibody that includes a protein sequence selected from the group consisting of SEQ ID Nos. 1-14, wherein at least a portion of any Chikungunya virus in the sample binds to the antibody, thereby producing a response from the immunoassay indicative of the presence of Chikungunya virus in the sample.

In a further embodiment, a method of inhibiting Chikungunya virus includes contacting Chikungunya virus with an antibody comprising a protein sequence is selected from the group consisting of SEQ ID No. 1 and SEQ ID No. 13.

An additional embodiment includes a nucleic acid encoding a single-domain antibody comprising a protein sequence selected from the group consisting of SEQ ID Nos. 1-14.

BRIEF DESCRIPTION OF THE DRAWINGS

FIG. 2 shows protein sequences of potential CHIKV-binding single domain antibodies.

FIG. 3 displays selected CHIKV-binding single domain antibody protein sequences.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

Figure 1:
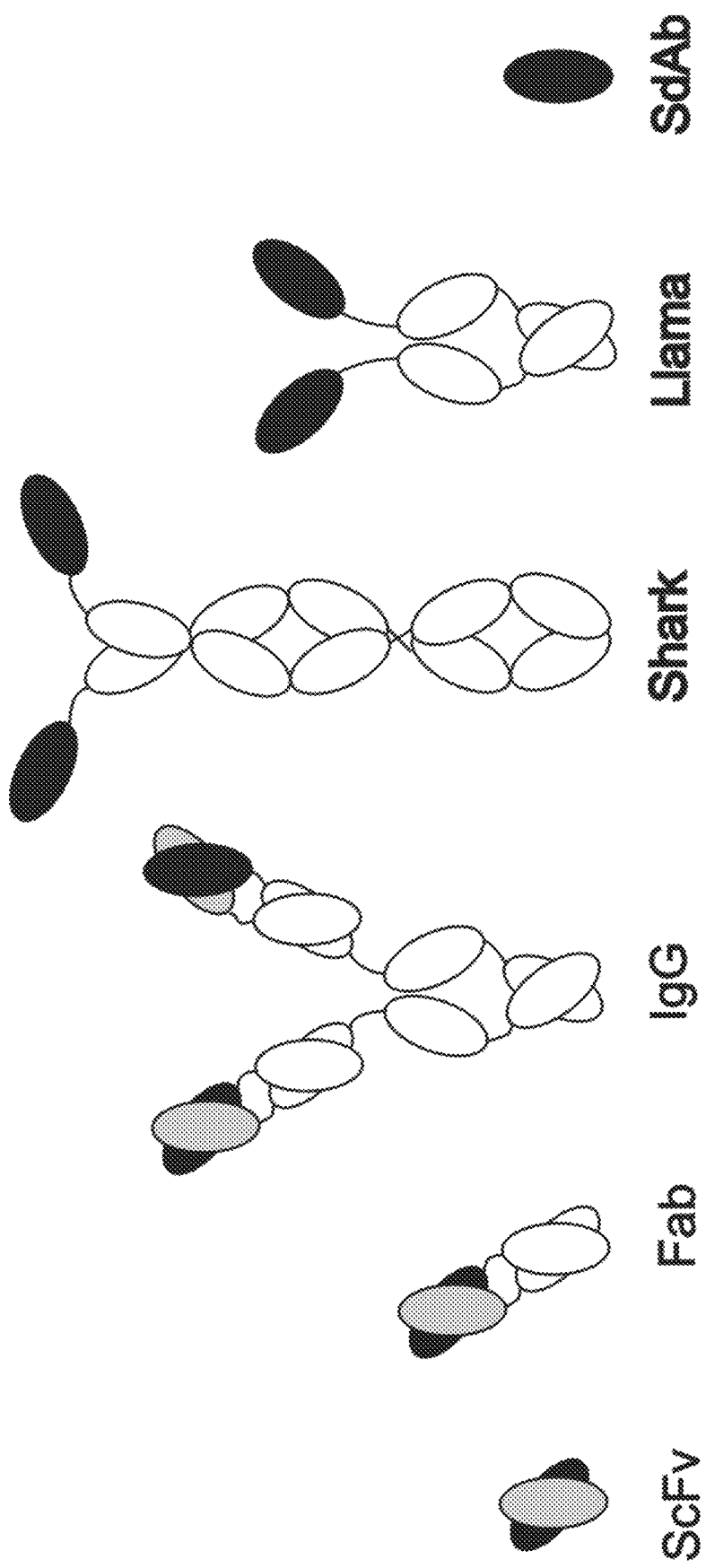
FIG. 1 is a schematic showing antibodies and recombinant derivatives. Other than sdAb, all those depicted exhibit a multi-domain nature. The heavy variable domains are shown in black, light domains in grey and the constant domains in white.

For detection applications many immunoassays rely on monoclonal or polyclonal antibodies (IgG) derived from mice, rabbits, goats, or sheep as recognition elements. Functional IgG are comprised of four polypeptide chains, two identical heavy (H) chains and two identical light (L) chains, linked by disulfide bonds. Each antibody has two antigen binding domains formed by the interaction of adjacent variable (V) domains from the H and L chains. The antigen binding surface is composed of six complementarity-determining regions (CDRs), three residing in each of the VH and VL protein domains. The interaction of these six CDR loops of varying sizes and sequences allows the formation of diversified antigen binding surfaces with the topologies to recognize a wide range of antigenic targets. Although sensitive and specific, conventional antibodies can be time-consuming and expensive to develop and have limited stability. FIG. 1 shows a schematic representation of IgG as well as the cloned binding derivative. Cloned derivatives of conventional IgG, comprising just the VH and VL domains to form a minimal antigen binding construct have been used as recognition elements for biosensor applications. These single chain antibodies (scFv) can be expressed in bacteria and modified by protein engineering to tailor the functionality and properties of the antibody fragments. ScFv, however, are often less stable than the parental full-length antibodies and just like full-length antibodies, they aggregate irreversibly at elevated temperatures due to their two-domain structure. Ideally, development of a single-domain structure capable of antigen binding would avoid aggregation upon heating and would facilitate the application of biosensors at elevated environmental temperatures or for continuous use over long periods of time.

Certain animals, such as camelids (i.e. camels, llamas) and sharks, possess a class of immunoglobulins consisting of heavy-chain homodimers where antigen binding is mediated through a single V domain. These V domains, when cloned as single domain antibodies (sdAb), comprise the smallest known antigen binding fragments (12-15 KDa). Despite their small size, sdAb display a high level of specificity and affinity for their antigens and have been shown to have nanomolar affinities (KD) for haptens and proteins. SdAb can re-fold to bind antigen after chemical or heat denaturation enabling them to retain the ability to bind antigen after exposure to elevated temperatures. Several studies have found sdAbs to be inherently thermostable, demonstrating antigen binding at elevated temperatures, which suggests they will be well suited for long-term field applications where refrigeration is often not possible. Recognition elements based on sdAb should offer the specificity of conventional antibodies with the potential for use and storage at elevated temperatures and the regeneration of sensor surfaces.

SdAb also offer several attractive features for therapeutic applications. Again their stability can make them stable at room temperature whereas most antibody therapeutics require refrigeration. Their small size means that the same weight of protein will have 5 times the specific activity and will diffuse much faster throughout the tissue. Its lack of an Fc domain may also be highly beneficial for the case of CHIKV therapeutics where the Fc mediated effects of the immune response appear to be responsible for much long term negative impact of CHIKV infection, namely the polyarthritis.

Examples

Llama-derived sdAb against Chikungunya Virus (E1 and virus like particles (VLPs)) were selected from a library originating from CHIKV VLP immunized animals. The binding ability of these isolated sdAb was characterized by a combination of surface plasmon resonance, enzyme linked immunosorbent assay (ELISA) and Luminex-based MagPlex assays. The sdAb were specific for either the E1 protein or bound both the E1 protein and VLPs. When two of these (CA6 and CC3) were tested in an assay to measure their ability to prevent the viral infection of Vero cells, both sdAb were effective in inhibiting cell infection. Single domain antibodies are often more stable than conventional antibodies and could be formulated to be delivered to resource limited areas that lack the refrigeration required for conventional immunoreagents.

Figure 2:
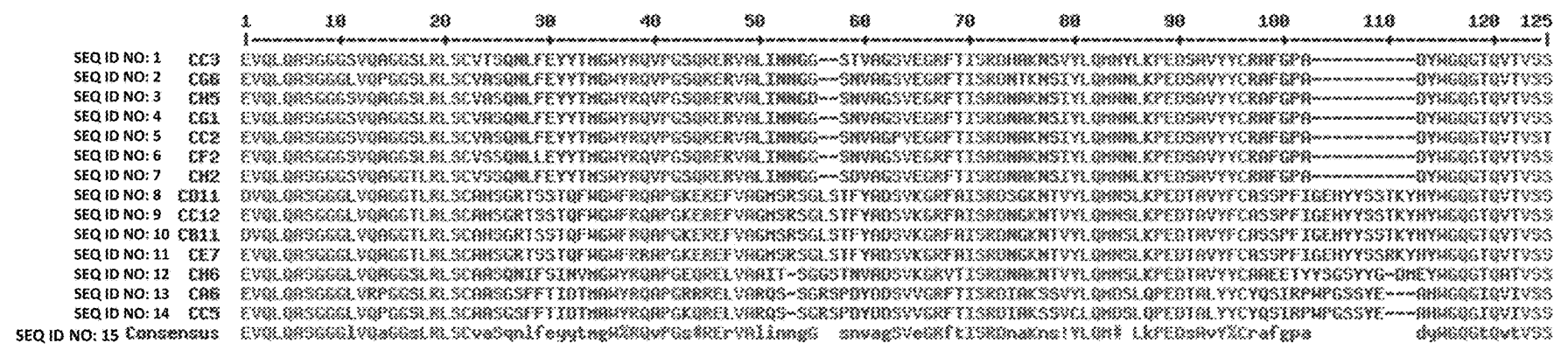

Fourteen sdAb were selected from a library constructed from immunized llamas (FIG. 2). They have the following sequences:

CC3 (SEQ ID No: 1):
EVQLQASGGGSVQAGGSLRLSCVTSQNLFEYYTMGWYRQVPGSQRERVA

LINNGGSTVAGSVEGRFTISRDHAKNSVYLQMNYLKPEDSAVYYCRAFG

PADYWGQGTQVTVSS

CG6 (SEQ ID No: 2):
EVQLQASGGGLVQPGGSLRLSCVASQNLFEYYTMGWYRQVPGSQRERVA

LINNGGSNVAGSVEGRFTISRDNTKNSIYLQMNNLKPEDSAVYYCRAFG

PADYWGQGTQVTVSS

CH5 (SEQ ID No: 3):
EVQLQASGGGSVQAGGSLRLSCVASQNLFEYYTMGWYRQVPGSQRERVA

LINNGDSNVAGSVEGRFTISRDNAKNSIYLQMNNLKPEDSAVYYCRAFG

PADYWGQGTQVTVSS

CG1 (SEQ ID No: 4):
EVQLQASGGGSVQAGGSLRLSCVASQNLFEYYTMGWYRQVPGSQRERVA

LINNGGSNVAGSVEGRFTISRDNAKNSIYLQMNNLKPEDSAVYYCRAFG

PADYWGQGTQVTVSS

CC2 (SEQ ID No: 5):
EVQLQASGGGSVQAGGSLRLSCVASQNLFEYYTMGWYRQVPGSQRERVA

LINNGGSNVAGPVEGRFTISRDNAKNSIYLQMNNLKPEDSAVYYCRAFG

PADYWGQGTQVTVST

CH2 (SEQ ID No: 6):
EVQLQASGGGSVQAGGTLRLSCVSSQNLFEYYTMSWYRQVPGSQRERVA

LINNGGSDVAGSVEGRFTISRDNAKNSIYLQMNNLKPEDSAVYYCRAFG

PADYWGQGTQVTVSS

CF2 (SEQ ID No: 7):
EVQLQASGGGSVQAGGSLRLSCVSSQNLLEYYTMGWYRQVPGSQRERVA

LINNGGSNVAGSVEGRFTISRDNAKNSIYLQMNNLKPEDSAVYYCRAFG

PADYWGQGTQVTVSS

CD11 (SEQ ID No: 8):
DVQLQASGGGLVQAGGTLRLSCAHSGRTSSTQFWGWFRQAPGKEREFVA

```
GMSRSGLSTFYADSVKGRFAISRDSGKNTVYLQMNSLKPEDTAVYFCAS

SPFIGEHYYSSTKYHYWGQGTQVTVSS

CC12 (SEQ ID No: 9):
EVQLQASGGGLVQAGGTLRLSCAHSGRTSSTQFWGWFRQAPGKEREFVA

GMSRSGLSTFYADSVKGRFAISRDNGKNTVYLQMNSLKPEDTAVYFCAS

SPFIGEHYYSSTKYHYWGQGTQVTVSS

CB11 (SEQ ID No: 10):
DVQLQASGGGLVQAGGTLRLSCAHSGRTSSTQFWGWFRQAPGKEREFVA

GMSRSGLSTFYADSVKGRFAISRDNGKNTVYLQMNSLKPEDTAVYFCAS

SPFIGEHYYSSTKYHYWGQGTQVTVSS

CE7 (SEQ ID No: 11):
EVQLQASGGGLVQAGGTLRLSCAHSGRTSSTQFWGWFRRAPGKEREFVA

GMSRSGLSTFYADSVKGRFAISRDNGKNTVYLQMNSLKPEDTAVYFCAS

SPFIGEHYYSSRKYHYWGQGTQVTVSS

CH6 (SEQ ID No: 12)
EVQLQASGGGLVQAGGSLRLSCAASQNIFSINVMGWYRQAPGEQRELVA

AITSGGSTNVADSVKGRVTISRDNAKNTVYLQMNSLKPEDTAVYYCAAE

ETYYSGSYYGDMEYWGQGTQATVSS

CA6 (SEQ ID No: 13):
EVQLQASGGGLVRPGGSLRLSCAASGSFFTIDTMAWYRQAPGRRRELVA

RQSSGRSPDYDDSVVGRFTISRDIAKSSVYLQMDSLQPEDTALYYCYQS

IRPWPGSSYEAHWGQGIQVIVSS

CC5 (SEQ ID No: 14):
EVQLQASGGGLVQPGGSLRLSCAASGSFFTIDTMAWYRQAPGKQRELVA

RQSSGRSPDYDDSVVGRFTISRDIAKSSVCLQMDSLQPEDTALYYCYQS

IRPWPGSSYEAHWGQGIQVIVSS
```

FIG. 2 shows an alignment of these sequences and a consensus sequence (SEQ ID NO: 15).

Figure 3:
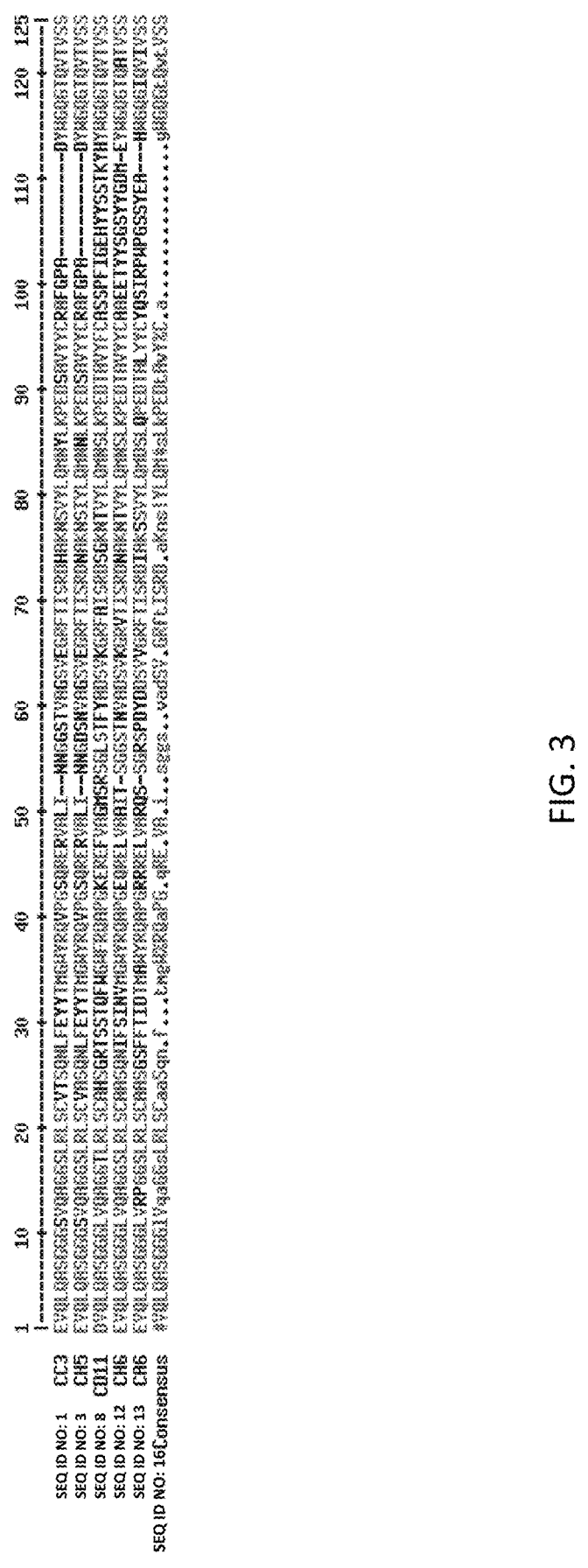

Five clones were selected from those four sequence families and deemed to be representative with regard to specificity and affinity (FIG. 3, including a consensus sequence with SEQ ID NO: 16). The binding affinity ($K_D$) was determined by surface plasmon resonance. The two binders shown have good affinity for CHIKV (low nM KD), with CC3 binding to the E1 protein immobilized in land 1 (L1) and the CHIKV VLP immobilized in lane 2 (L2), while CA6 was only observed to bind to the E1 protein in this assay.

Figure 4A:
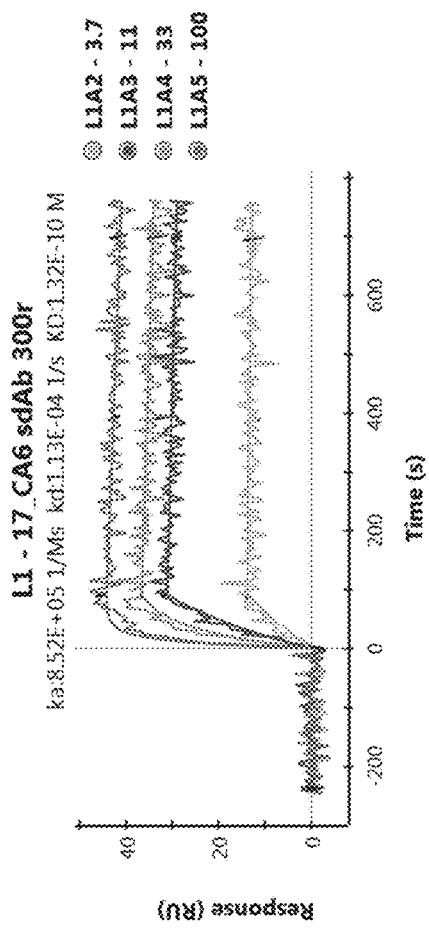
FIGS. 4A-4C provide plasmon resonance binding affinity data.
Figure 4B:
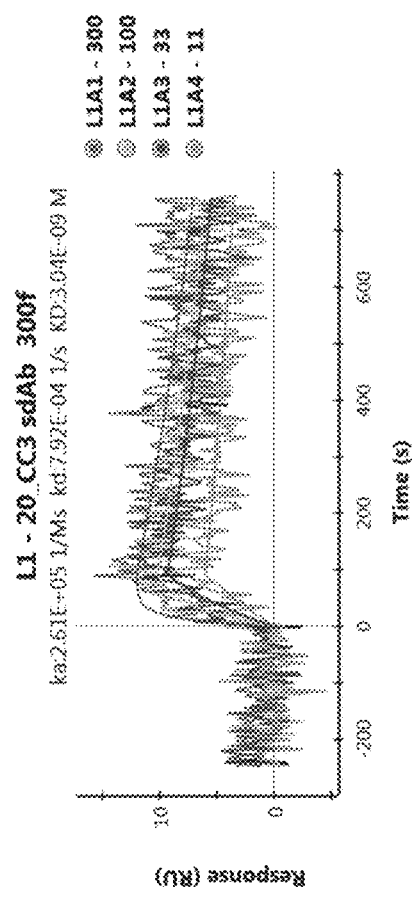
Figure 4C:
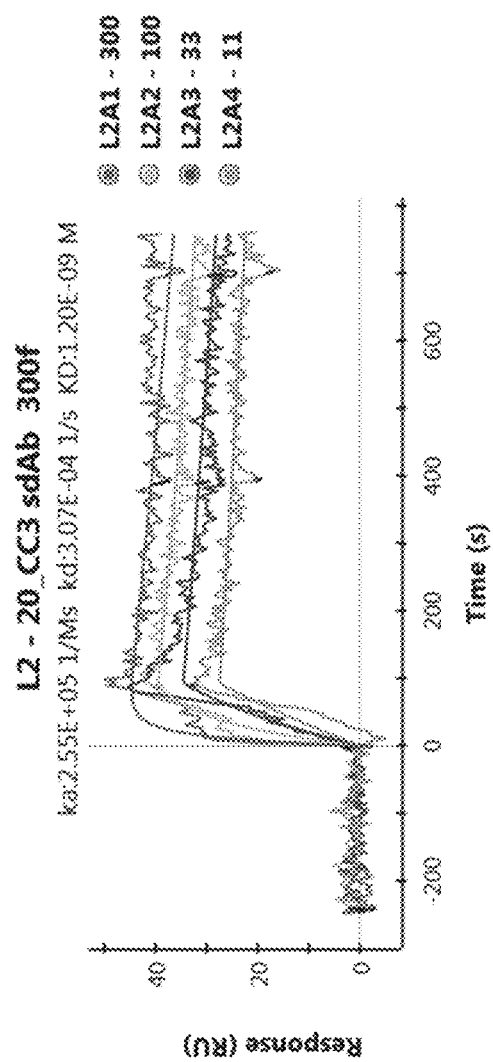

The binding affinity (KD) for all the binders was determined by surface plasmon resonance. The two binders shown have good affinity for CHIKV (low nM KD), with CC3 binding to the E1 protein immobilized in land 1 (L1) and the CHIKV VLP immobilized in lane 2 (L2), while CA6 was only observed to bind to the E1 protein in this assay. These data are provided in FIGS. 4A-4C.

Figure 5B:
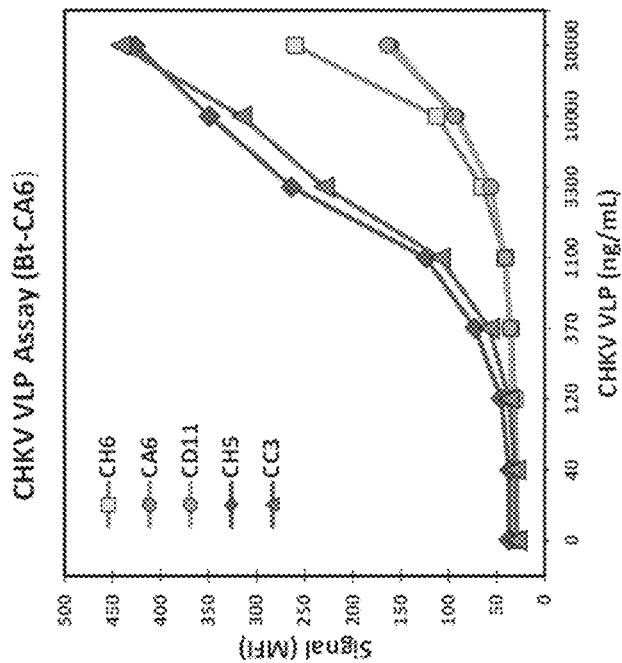
FIGS. 5A and 5B present results of a MagPlex Sandwich assay for CHIKV VLPs using sdAb.
Figure 5A:
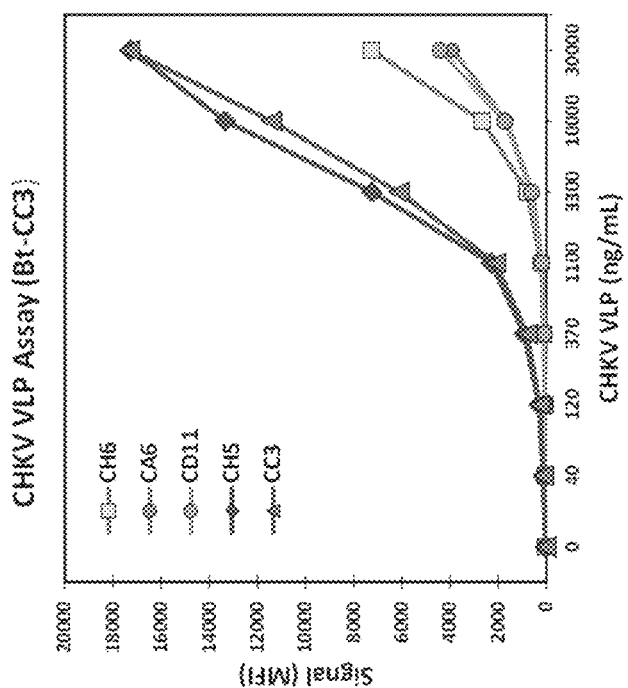

MagPlex sandwich immunoassays were used for CHIKV VLPs using all five of the prepared sdAb. This showed that using both CC3 and CA6 as the biotinylated tracer that CC3 and the other member of that family CH5 acted as the strongest capture sdAb for the CHIKV VLPs as seen in FIGS. 5A and 5B.

Figures 6A, 6B:
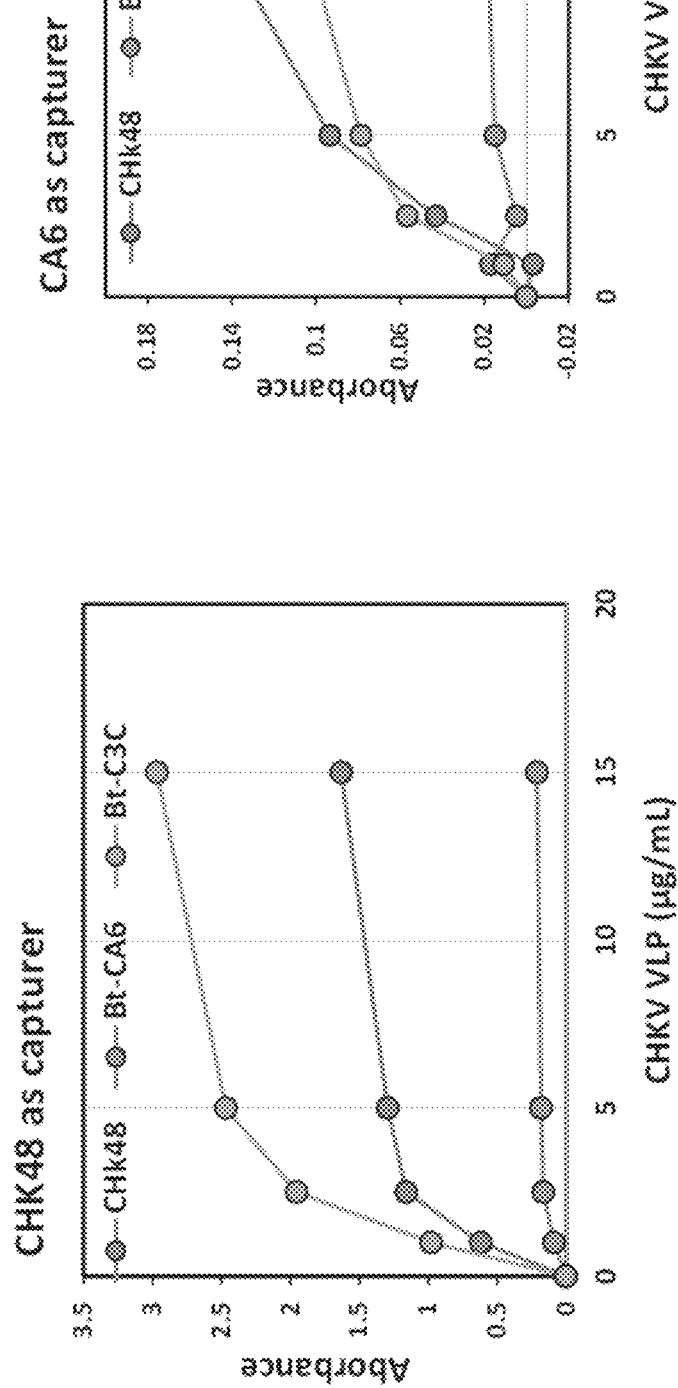
FIGS. 6A-6C show results of an enzyme-linked immunosorbent assay (ELISA) assay for CHIKV VLPs using sdAbs and a monoclonal CHK48.
Figure 6C:
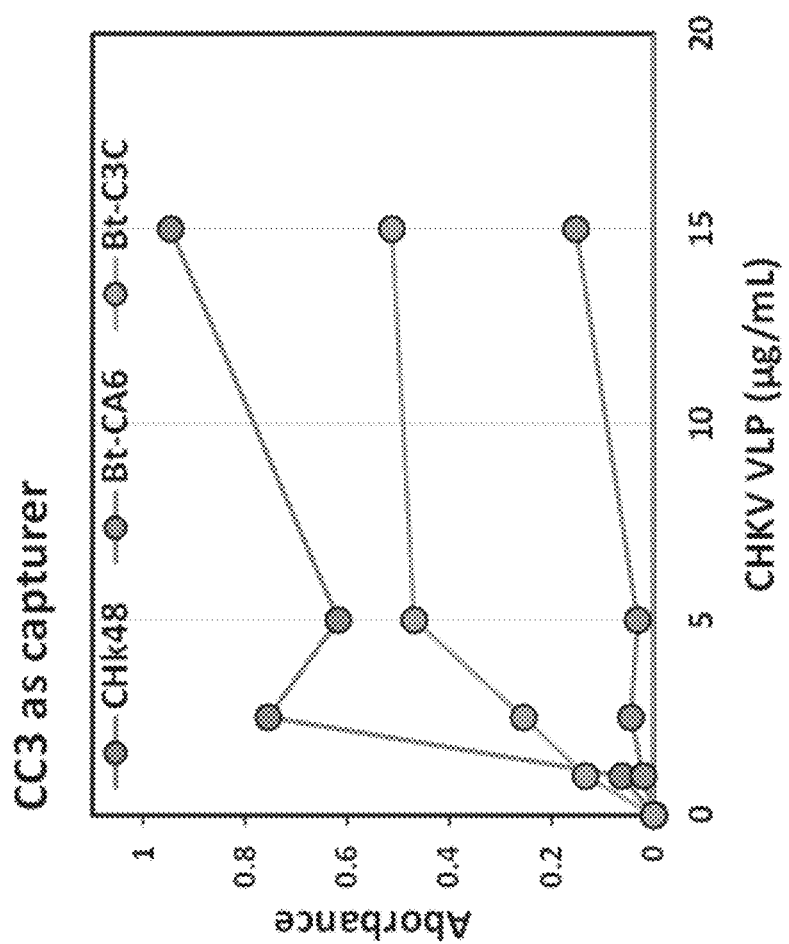

ELISAs were also evaluated using CA6 and CC6 along with an anti CHIKV monoclonal antibody (CHK48) to demonstrate they would work in this format. FIGS. 6A-6C show that, as in the MagPlex assay, CC3 (also called C3C) performed better than CA6.

The ability of the sdAb to inhibit the CHIKV was examined. Twelve two-fold serial dilutions of each sdAb (CC3, 39 μg/mL and CA6, 10 μg/mL) starting at the respective concentrations were prepared. Each dilution was incubated with ~300 plaque forming units (PFU) of CHIKV in duplicate for one-hour inoculation. The compound-virus mix was then added to Vero cells seeded in 24-well culture plates for one-hour incubation, followed by adding 0.8% methylcellulose to each well and incubating for three days at 37° C. in a humidified 5% CO2 atmosphere.

Figure 7B:
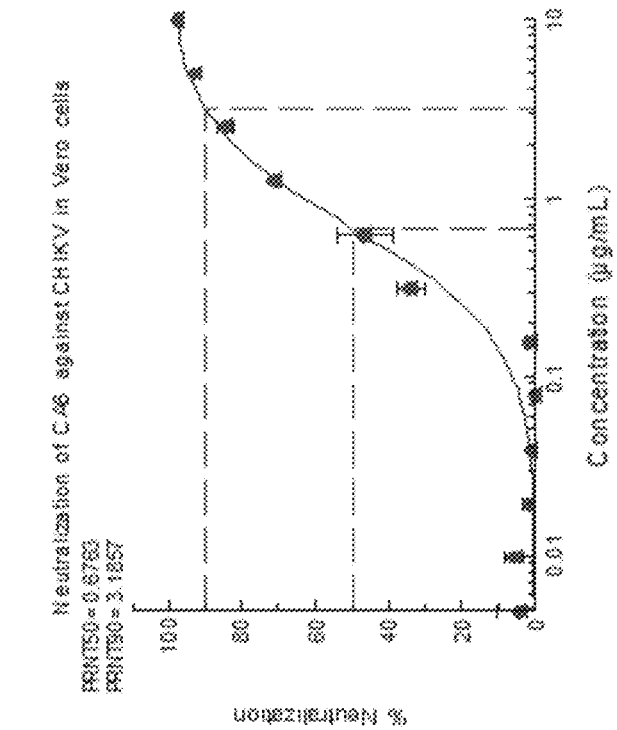
FIGS. 7A and 7B show CC3 and CA6 dose dependent inhibition of Vero cell infection by CHIKV.
Figure 7A:
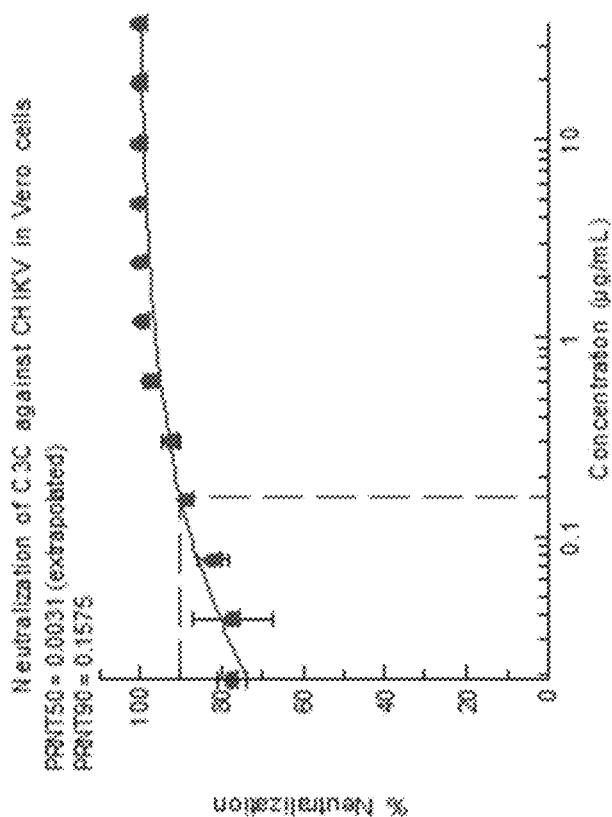

On day three post incubation, the Vero cells were fixed and infected foci were counted by using crystal violet staining. 50 percent plaque reduction neutralization titer (PRNT50) of each compound was calculated using XLfit dose response model. The results, seen in FIGS. 7A and 7B, show that CC3 (C3C) is highly effective at inhibiting the infection of Vero cells by CHIKV. CA6 was also effective, but required higher doses to do so.

Further Embodiments

Also contemplated herein are additional antibodies that incorporate the consensus sequences of FIGS. 2 and 3.

In addition to the assays used in the above examples, other assays incorporating anti-CHIKV sdAbs are contemplated. Such assays might be used, for example, to detect whether a patient might be infected with CHIKV.

It is further contemplated that such antibodies might be active ingredients in treatments for CHIKV infection.

Advantages

These new sequences represent rugged detection reagents that have potential uses as therapeutics. Whereas conventional antibodies will require cold storage and cannot be easily tailored to work optimally with various detection platforms, sdAb are rugged binding molecules can be engineered to be even more thermally stable if need be, but they naturally have robust stability being able to refold if denatured, and they can also be expressed with a variety of fusion domains to enhance their utility. In addition, one of the lasting problems associated with CHIKV infection is the instigation of long lasting arthritic conditions, while it is unclear if these sdAb could help prevent that sequelae, they are an attractive alternative to be investigated.

Concluding Remarks

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

Pal P, Dowd K A, Brien J D, Edeling M A, Gorlatov S, et al. (2013) "Development of a Highly Protective Combination Monoclonal Antibody Therapy against Chikungunya Virus." PLoS Pathog 9(4): e1003312. doi:10.1371/journal.ppat.1003312

Warter L, Lee C Y, Thiagarajan R, Grandadam M, Lebecque S, et al. "Chikungunya Virus Envelope-Specific Human Monoclonal Antibodies with Broad Neutralization Potency." J Immunol 186 (5), 2011.

Rebecca Broeckel R, Fox J M, Haese N, Kreklywich C N, Sukulpovi-Petty S, et al. "Therapeutic administration of a recombinant human monoclonal antibody reduces the severity of chikungunya virus disease in rhesus macaques" PLoS Negl Trop Dis 11(6): e0005637, 2017.

US 2016/0145323A1 "Antibodies against chikungunya virus and uses thereof," Doranz B, Mattia K, Kahle K, Simmons G. May 26, 2016

What is claimed is:

1. A nucleic acid encoding a single-domain antibody comprising a protein sequence selected from the group consisting of SEQ ID Nos: 1-14.

2. The nucleic acid of claim 1, wherein the protein sequence is selected from the group consisting of SEQ ID No: 1 and SEQ ID No: 13.

3. A nucleic acid encoding a single-domain antibody comprising a protein sequence having SEQ ID No: 1.

\* \* \* \* \*